United States Patent [19]

Lukas et al.

[11] Patent Number: 4,465,666
[45] Date of Patent: Aug. 14, 1984

[54] NEW PHARMACEUTICAL PREPARATIONS

[75] Inventors: Bohumir Lukas, Basel; Walter Wiesendanger, Münchenstein; Karl H. Schmidt-Ruppin, Arlesheim, all of Switzerland

[73] Assignee: Ciba-Geigy Corporation, Ardsley, N.Y.

[21] Appl. No.: 316,585

[22] Filed: Oct. 30, 1981

Related U.S. Application Data

[63] Continuation of Ser. No. 112,593, Jan. 16, 1980, abandoned, which is a continuation of Ser. No. 966,700, Dec. 5, 1978, abandoned, which is a continuation-in-part of Ser. No. 915,697, Jun. 15, 1978, abandoned.

[30] Foreign Application Priority Data

Jun. 17, 1977 [LU] Luxembourg ............................ 77562

[51] Int. Cl.$^3$ .................... A61K 33/30; A61K 31/70; A61K 31/725; A61K 31/555; A61K 31/315; A61K 31/74
[52] U.S. Cl. ..................................... 424/145; 424/78; 424/180; 424/183; 424/245; 424/289
[58] Field of Search ................ 424/183, 145, 180, 78, 424/245, 289

[56] References Cited

FOREIGN PATENT DOCUMENTS 133 9/1981 European Pat. Off. .
2715711 10/1978 Fed. Rep. of Germany ...... 424/145

OTHER PUBLICATIONS

Chemical Abstracts 65: 10845h–10846h (1965).
Chemical Abstracts 83: 136936f (1975).
Chemical Abstracts 66: 45191s (1967).
Carcinogensis Abstracts, vol. XIV, No. 11, Nov. 1976, p. 976 (No. 6316).
The Merck Index, 8th ed., Merck & Co. Inc., Rahway, N.J., 1968, pp. 848–849.

Primary Examiner—Jerome D. Goldberg
Attorney, Agent, or Firm—Irving N. Feit

[57] ABSTRACT

The invention relates to new pharmaceutical preparations for the topical treatment of infections caused by herpes viruses, especially those which have been caused by herpes virus hominis, for example of herpes genitalis and herpes dermatitis. The preparations contain as antiviral agent a synergistic combination of an acid sulphated polysaccharide or acid sulphated polymer, in particular heparin, and zinc ions, and may further contain polyoxyethylene sorbitan monolaurate and/or -monooleate. They are usual types of preparations for topical administration such as tinctures, solutions, creams, ointments and, especially, gels.

22 Claims, No Drawings

NEW PHARMACEUTICAL PREPARATIONS

This is a continuation of application Ser. No. 112,593 filed Jan. 16, 1980, now abandoned, which in turn is a continuation of application Ser. No. 966,700, filed Dec. 5, 1978, now abandoned, which in turn is a continuation-in-part of application Ser. No. 915,697, filed June 15, 1978, now abandoned.

The invention relates to new pharmaceutical preparations for topical administration, especially for the topical treatment of virus infections, which contain an effective antiviral combination of an acid sulphated polysaccharide or acid sulphated polymer, in particular heparin, and zinc ions, and to the use of said preparations for the topical treatment of infections caused by herpes viruses, especially those which have been caused by herpes virus hominis (HVH), for example of herpes genitalis and herpes dermatitis.

The surprising discovery has been made that acid sulphated polysaccharides or acid sulphated polymers, in particular heparin, and zinc ions together exert a strong antiviral action which far exceeds the sum of the action of each of the individual components. The synergistic action of both components can be ascertained in vitro, i.e. in cell cultures, for example on the basis of the virus inactivation, of the inhibition of plaque formation and of the virus replication.

1. Inactivation of herpes virus hominis

The preparations, mixed in bidistilled water in graduated concentrations, were inoculated with HVH2/Ang. and incubated for 1 hour at 35° C. The determination of the virus content in the contact mixtures was made on chicken embryo fibroblasts in the plaque test. The samples, diluted in Hank's solution with 0.05% of albumin, were added to cell monolayers of chicken embryo fibroblasts. After 90 minutes virus absorption, the cultures were washed twice, treated with 4 ml of LY-agar overlay [Hank's solution with 0.5% of lactalbumin hydrolysate and 0.01% of yeastolate (yeast extract)] and then incubated at 35° C. until the plaques were counted (36 hours).

TABLE I

| ZnSO$_4$.7H$_2$O | Preparations, mcg/ml: heparin (sodium salt)* | | |
|---|---|---|---|
| | 0 | 33 | 100 |
| 0 | 5.10[1] | 5.04 | 5.00 |
| 33 | 4.89 | 4.76 | 4.95 |
| 100 | 4.76 | 2.60 | 2.62 |
| 300 | 4.68 | <1.00 | <1.00 |

[1]Virus content: Log 10 PFU/ml (plaque forming units/ml)
*160 IU/mg (Biofac AS, Copenhagen, Denmark)

2. Inhibition of the plaque formation of HVH2/Ang. in chicken embryo fibroblasts The cell monolayers were infected with 100 PFU of HVH2/Ang. over the course of 90 minutes. 4 ml of each of the preparations incorporated in LY-agar overlay (with 5% of sheep serum, 0.5% of OXO-L-28-agar, without diethylaminoethyl dextrane) were added to the infected cell cultures, which were incubated at 35° C. until the plaques were counted (96 hours).

TABLE II

| ZnSO$_4$.7H$_2$O | Preparations, mcg/ml: heparin (sodium salt)* | | | |
|---|---|---|---|---|
| | 0 | 1,5 | 3 | 6 |
| 0 | 100[1] | 82 | 87 | 76 |
| | 2–3[2] | 2–3 | 2–3 | 1–2 |
| 3 | 104 | 65 | 57 | 42 |
| | 1–3 | 1–2 | 0.5–1 | 0.5 |
| 6 | 64 | 31 | 11 | 2 |
| | 1–2 | 0.5–1 | 0.5 | 0.5 |
| 12 | 43 | 8 | 2 | 2 |
| | 0.5–1 | 0.5 | 0.5 | 0.5 |
| 25 | 15 | 5 | 2 | 1 |
| | 0.5 | 0.5 | 0.5 | 0.5 |

[1]number of plaques of 3 dishes in %
[2]diameter of plaques in mm (approx.)
*160 IU/mg (Biofac)

3. Inhibition of the replication of HVH2/Ang. in VERO cells on pre-infective commencement of treatment Confluent monolayers of VERO cells were washed with F15-medium [Minimum Essential Medium (Eagle), Gibco Bio-Cult Ltd., Paisley, Scotland], and then covered with 4 ml of each of the different concentrations of the preparations in F15 medium. The cultures were infected after 60 minutes with 1000 PFU of HVH2/Ang. in 0.1 ml of medium. After an incubation of 20 hours at 35° C., the state of the cells was assessed microscopically and the virus content of the cell lysates (cells with 1 ml of bidistilled water, deep frozen twice and thawed) determined by titration on chicken embryo fibroblasts (evaluation of the plaque formation).

TABLE III

| ZnSO$_4$.7H$_2$O | Preparations, mcg/ml: heparin (sodium salt)* | |
|---|---|---|
| | 0 | 6 |
| 0 | 4.58[1] | 1.84 |
| 6 | 3.59 | <1.00 |
| 12 | 3.32 | <1.00 |
| 25 | 2.82 | <1.00 |

[1]Log 10 PFU/ml cell lysate
*160 IU/mg (Biofac)

Conclusions drawn from the results of the three series of tests

In the above experimental procedures, the synergistic action of the combinations of zinc sulphate and heparin of the present invention can be clearly observed. Especially noteworthy in the virus inactivation according to Table I is the fact that each component by itself in all tested concentrations was virtually inactive, whereas the combination of one third of the maximum concentration of each of the individual components reduced the virus content of the chicken embryo fibroblasts by $10^2$. Table II shows, inter alia, that heparin by itself has only a weak action, but both heparin and zinc sulphate in the lowest concentration, together with each concentration of the second component, have a stronger action than the next highest concentration of the second component by itself. The action of 25 mcg/ml of zinc sulphate by itself is achieved with the combination of 6 mcg/ml of zinc sulphate and 3 mcg/ml of heparin, and the action of the combination of 25 mcg/ml of zinc sulphate and 6 mcg/ml of heparin is almost achieved with 6 mcg/ml of zinc sulphate and 6 mcg/ml of heparin and also with 12 mcg/ml of zinc sulphate and 3 mcg/ml of heparin. Table III shows that the virus replication is only moderately inhibited by zinc sulphate in the highest concentration of 25 mcg/ml, but, on account of the strong absorption inhibiting action of heparin, is clearly inhibited by heparin in the single tested concentration of 6 mcg/ml, corresponding to the highest concentration in the other test series. All tested combinations, however, exhibit an action at least 10 times stronger than that of the single components.

It is also possible to determine the synergistic effect of the combined active substances in vivo, in the treatment commencing 72 hours after infection (stage of clear symptoms), of female guinea pigs with herpes genitalis caused by intravaginal infection with HVH2/Ang., according to the method described by B. Lukas et al., Arch. Ges. Virusforsch. 44, 153–155 (1974) and 49, 1–11 (1975). The results of correponding double blind tests are given in the following table IV.

TABLE IV

| Preparation | | | Effect on local symptoms[b] | | | | | | | | | Para- lysis % | Ex- itus % |
|---|---|---|---|---|---|---|---|---|---|---|---|---|---|
| | | | % Animals with regression >66% at day | | | | % Animals free of symptoms at day | | | | | | |
| No. | H IU/g | Z % | n[a] | 4 | 7 | 9 | 11 | 9 | 11 | 14 | 18 | 25 | | |
| 1 | — | —[c] | 108 | 0 | 0 | 3 | 6 | 2 | 3 | 5 | 9 | 15 | 39 | 24 |
| 2 | — | —[d] | 35 | 0 | 11 | 17 | 37 | 14 | 25 | 40 | 48 | 51 | 23 | 11 |
| 3 | 32 | — | 8 | 0 | 0 | 25 | 37 | 0 | 12 | 25 | 37 | 62 | 0 | 0 |
| 4 | 160 | — | 36 | 0 | 11 | 39 | 61 | 30 | 30 | 41 | 58 | 66 | 8 | 3 |
| 5 | — | 0,5 | 10 | 0 | 0 | 10 | 10 | 0 | 10 | 30 | 50 | 70 | 20 | 0 |
| 6 | — | 1,0 | 18 | 0 | 5 | 5 | 17 | 0 | 17 | 28 | 33 | 33 | 11 | 5 |
| 7 | 32 | 0,5 | 10 | 10 | 10 | 30 | 40 | 0 | 10 | 50 | 40 | 40 | 20 | 0 |
| 8 | 32 | 1,0 | 10 | 0 | 0 | 30 | 20 | 20 | 20 | 30 | 50 | 80 | 0 | 0 |
| 9 | 160 | 0,5 | 19 | 0 | 5 | 84 | 94 | 53 | 72 | 94 | 94 | 94 | 10 | 5 |
| 10 | 160 | 1,0 | 46 | 6 | 37 | 63 | 87 | 43 | 74 | 78 | 87 | 90 | 4 | 0 |

H = Heparin sodium salt, 160 IU/mg (Biofac)
Z = ZnSO$_4$.7H$_2$O
[a]Numbers of animals >10 are total numbers of test animals of several tests with groups of 8 or 10 animals
[b]Day 0 is day of start of treatment 72 hours after infection. The treatment consists in intravaginal administration of 0,1 ml of the preparation to be tested twice per day for 5 subsequent days
[c]Control animals receiving no treatment
[d]Control animals treated with gel base used for all preparations and containing 0,1% polyoxyethylene sorbitan monooleate.

The results of the comparative tests show that administration of either heparin or zinc ions alone as active ingredient in a suitable gel base gives rise to only a moderate increase of the beneficial effect of the gel base alone, as is demonstrated by the fact that, at most, about 70% of the test animals are free of symptoms at the end of the test period when already about 50% of the animals treated with the gel base are free of symptoms. In contradistinction thereto, the combined administration of zinc ions and heparin within the range of concentration according to the invention results in almost a complete cure of the experimental disease, with 18 out of 19, or 42 out of 46, test animals respectively, i.e. at least 90%, being free of symptoms at the end of the test period. Moreover, the early onset of the curative action perceptible after administration of the higher dosage of heparin alone is also markedly enhanced after administration of the combination, although after the administration of zinc ions alone the onset of the action is slow.

The synergistic action of the above active substances is further increased by using a preparation base, especially a gel base, which contains one or more polyoxyethylene sorbitan fatty acid esters, such as polyoxyethylene sorbitan monostearate and/or, in particular, polyoxyethylene sorbitan monolaurate, or most preferably, polyoxyethylene sorbitan monooleate.

The pharmaceutical preparations of the present invention contain the above defined active substances preferably in combination with pharmaceutical adjuvants suitable for topical application. Suitable formulations of preparations of the invention are in particular tinctures, solutions, creams, ointments and, especially, gels.

Tinctures and solutions generally have an aqueous ethanolic base to which are added, inter alia, polyalcohols, for example propylene glycol or glycerin, and/or lower polyethylene glycols, as humectants for reducing water loss, and fat-restoring substances, such as fatty acid esters of lower polyethylene glycols, i.e. lipophilic substances which are soluble in the aqueous-ethanolic mixture as substitute for fatty substances which are taken from the skin with the ethanol, and, if necessary, other assistants and adjuvants, in addition to conventional preservatives, such as those mentioned hereinbelow, for example also the polyoxyethylene sorbitan fatty acid esters already mentioned, such as polyoxyethylene sorbitan monolaurate or polyoxyethylene sorbitan monooleate.

Creams are oil-in-water emulsions which contain more than 50% of water. Fatty alcohols are chiefly used as oleaginous base, for example lauryl, cetyl or stearyl alcohol, fatty acids, for example palmitic or stearic acid, liquid to solid waxes, for example isopropyl myristinate, wool wax or bees-wax, and/or hydrocarbons, for example petroleum jelly (petrolatum) or paraffin oil. Suitable emulsifiers are surface-active substances with primarily hydrophilic properties, such as corresponding non-ionic emulsifiers, for example fatty acid esters of polyalcohols or ethylene oxide adducts thereof, such as polyglycerin fatty acid esters or polyoxyethylene sorbitan fatty acid esters (Tweens); polyoxyethylene fatty alcohol ethers or esters; or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol. Additives to the water phase include agents which reduce water less through evaporation, for example polyalcohols, such as glycerin, sorbitol propylene glycol and/or polyethylene glycols, as well as preservatives, perfumes etc.

Ointments are water-in-oil emulsions which contain up to 70%, preferably however about 20% to about 50%, of water or aqueous phase. The oleaginous phase comprises chiefly hydrocarbons, for example petroleum jelly, paraffin oil and/or hard paraffins, which contain preferably hydroxy compounds suitable for improving the water-absorption, such as fatty alcohols or esters thereof, for example cetyl alcohol or wool wax alcohols, or wool wax. Emulsifiers are corresponding lipophilic substances, such as sorbitan fatty acid esters (Spans), for example sorbitan oleate and/or sorbitan isostearate. Additives to the water phase include humectants, such as polyalcohols, for example glycerin, propylene glycol, sorbitol and/or polyethylene glycol, and preservatives, perfumes etc.

Gels are in particular aqueous solutions of the active substances in which gel formers, preferably those of the group of cellulose ethers, for example methyl cellulose, hydroxyethyl cellulose or carboxymethyl cellulose, or of the vegetable hydrocolloids, such as sodium alginate, tragacanth or gum arabic, are dispersed and swelled. The gels preferably also contain in addition humectants from the group of the polyalcohols, such as propylene glycol, glycerin and/or lower polyethylene glycols, as well as wetting agents, for example polyoxyethylene sorbitan fatty acid esters, such as polyoxyethylene sorbitan monostearate, monolaurate or monooleate, in concentrations of about 0.02 to 5%. As further adjuvants, the gels contain conventional preservatives, for example benzyl alcohol, phenethyl alcohol, phenoxyethanol, lower alkyl esters of p-hydroxybenzoic acid such as the methyl and/or propyl esters, sorbic acid or organic mercury compounds such as merthiolate.

In addition to containing the conventional preservatives, the preparations of the present invention can also contain further biological, for example antiphlogistic or antimicrobial, such as antibacterial, antifungal or also antiviral, active substances, for example flumethasone, neomycin, gentamycin, lactic acid or mikonazole. The preparations of the invention are formulated in a manner which is in itself known.

The present invention relates in particular to antiviral preparations for topical application which contain acid sulphated polysaccharides or acid sulphated polymers, such as heparin, and zinc ions, in a ratio of 1 mg to 0.18 up to 18 mg, especially of 1 mg to 0.18 up to 4.5 mg, and optionally polyoxyethylene sorbitan monolaurate and/or monooleate. For heparin, the above amounts refer to that having 160 IU/mg; equal IU amounts of other heparin will be used. The zinc ions are added in the form of the corresponding amounts of a dissociable zinc compound, for example of 0.8 to 80 mg, or 0.8 to 20 mg respectively of $ZnSO_4.7H_2O$. Corresponding preparations for topical application, especially gels, and also tinctures, aqueous solutions, creams or ointments, contain for example, per gram or milliliter, 0.1 to 5 mg, in particular 0.25 to 3 mg of an acid sulphated polysaccharide or acid sulfated polymer, corresponding to 16 to 800 IU, in particular to 40 to 480 IU of heparin, and 0.18 to 18 mg of zinc ions, corresponding for example to about 0.8 to 80 mg of $ZnSO_4.7H_2O$, and optionally in addition 0.2 to 50 mg of polyoxyethylene sorbitan monolaurate and/or monooleate.

A content of 80 to 320 IU of heparin, 0.45 to 4.5 mg of zinc ions and optionally in addition 0.5 to 10 mg of polyoxyethylene sorbitan monolaurate and/or monooleate, per gram or milliliter, is particularly preferred.

Instead of heparin, it is also possible to use an equally effective antiviral amount of another acid sulphated polysaccharide or of an acid sulphated polymer. By acid sulphated polysaccharides are understood polysaccharides wherein monovalent sulphuric acid radicals —$SO_2$—OH are linked with oxygen atoms and/or, if present, as in the case of heparin, nitrogen atoms. Such acid sulphated polysaccharides may be of natural origin, such as heparin, chondroitin sulphate (chondroitinsulphuric acid) or carregeenan, or may be obtained by sulphation of natural or partially degraded polysaccharides, such as sulphated amylopectins, sulphated dextrans, sulphated polyglucoses or sulphated polypentoses, preferably in the form of suitable pharmaceutically acceptable salts, such as e.g. potassium and especially sodium salts. Special reference is made in this regard to the sodium salt of heparin as the commonly used commercial form of heparin, also the potassium salt and the magnesium salt of heparin, the sodium salts of dextran sulphates and the sodium salt of the calcium complex of the sulphation product of oxidatively degraded methyl ester of polygalacturonic acid [active substance of HEMERAN (Geigy)]. Acid sulphated polymers are sulphation products of polymers containing hydroxy groups, such as e.g. acid sulphated polyvinyl alcohol (polyvinyl sulphate), which again is used preferably in the form of a pharmaceutically acceptable salt, such as the sodium or potassium salt.

Instead of being added in the form of zinc sulphate, the zinc ions can also be added in the form of another dissociable zinc compound, for example zinc chloride, zinc acetate or zinc citrate, or of the zinc salt of an acid or another substance of acidic character and having its own biological, for example antibacterial or antiphlogistic, properties, for example zinc sudoxicam (zinc salt of 4-hydroxy-2-methyl-N-(2-thiazolyl)-1,2-benzothiazine-3-carboxamide-1,1-dioxide).

The preparations of the present invention are especially suitable for the treatment of herpes genitalis, herpes dermatitis and herpes labialis. For treating the first two infections, gels formulated according to the invention are applied as early as possible, for example from a tube or dispenser, 2 to 3 times daily, and for treating herpes labialis, are applied several times daily to the infected parts of the body until the symptoms disappear and the infection heals. Aqueous solutions formulated according to the invention can be used for example for washing infected body cavities, especially for treating herpes gingivostomatitis or herpes keratoconjunctivitis.

The following Examples describes the manufacture of typical formulations, without implying any restriction of the scope of the invention.

EXAMPLE 1

To prepare 10 liters of gel, 200 g of highly viscous sodium carboxymethyl cellulose and 50 g of polyoxyethylene sorbitan monostearate (TWEEN 60) are mixed with 1000 g of glycerin and 6.5 liters of aqua conservans and the mixture is allowed to swell to a homogeneous mucilage. Then a solution of $1.6 \cdot 10^6$ international units of sodium salt of heparin (e.g. 10 g of heparin Biofac), 100 g of zinc sulphate heptahydrate and 10 g of polyoxyethylene sorbitan monooleate (TWEEN 80) in 2 liters of aqua conservans is added. Finally, the mixture is bulked to 10 liters with aqua conservans, carefully mixed and tubes are filled with the resulting gel.

By aqua conservans is meant an aqueous solution of 0.07% of p-hydroxybenzoic acid methyl ester (methyl paraben) and 0.03% of p-hydroxybenzoic acid propyl ester (propyl paraben). TWEEN 60 and TWEEN 80 are registered trademarks of ICI of America Inc., Stamford, Conn. 06904.

Instead of using 100 g of ZnSO$_4$.7H$_2$O, it is also possible to use 50 g and to repeat the above procedure.

EXAMPLE 2

The procedure of Example 1 is repeated, using instead of heparin 5.0 g of the sodium salt of dextran sulphate of a molecular weight of about 48,000.

EXAMPLE 3

The procedure of Example 1 is repeated, using instead of heparin 2.5 g of the sodium salt of dextran sulphate of the molecular weight of about $2 \cdot 10^6$.

EXAMPLE 4

The procedure of Example 1 is repeated, using instead of heparin 2.5 g of the potassium salt of polyvinyl sulphate of a molecular weight of about 80,000.

What is claimed is:

1. Pharmaceutical preparation for topical administration comprising an anti-viral effective amount of an acid sulfated polysaccharide or acid sulfated polymer selected from the group consisting of heparin, dextran sulfate and polyvinyl sulfate; and zinc ions in the form of a dissociable zinc compound in a weight ratio of acid sulfated polysaccharide or acid sulfated polymer to zinc ions of 1:0.18 to 4.5 together with pharmaceutical adjuvants suitable for topical application.

2. Pharmaceutical preparation according to claim 1 wherein the acid sulphated polysaccharide or acid sulphated polymer is present in the form of a pharmaceutically acceptable salt.

3. Pharmaceutical preparation according to claim 2 wherein the pharmaceutically acceptable salt is heparin.

4. Pharmaceutical preparation according to claim 2 wherein the pharmaceutically acceptable salt is dextran sulfate.

5. Pharmaceutical preparation according to claim 2 wherein the pharmaceutically acceptable salt is polyvinyl sulfate.

6. Pharmaceutical preparation according to claim 1 which additionally contains at least one surface active agent selected from polyoxyethylene sorbitan monolaurate and polyoxyethylene sorbitan monooleate.

7. Pharmaceutical preparation according to claim 1 which contains heparin and zinc ions in a ratio of 160 IU to 0.18 to 18 mg.

8. Pharmaceutical preparation according to claim 1 which contains, per gram or milliliter, 0.1 to 5 mg of an acid sulphated polysaccharide or acid sulphated polymer and 0.18 to 18 mg of zinc ions.

9. Pharmaceutical preparation according to claim 8 which contains, per gram or milliliter, 16 to 800 IU of heparin and 0.18 to 18 mg of zinc ions.

10. Pharmaceutical preparation according to claim 8 which contains, per gram or milliliter, 40 to 480 IU of heparin and 0.18 to 18 mg of zinc ions.

11. Pharmaceutical preparation according to claim 10 which additionally contains, per gram or milliliter, 0.5 to 10 mg of a surface active agent selected from polyoxyethylene sorbitan monolaurate and polyoxymethylene sorbitan monooleate.

12. Pharmaceutical preparation according to claim 8 to which the zinc ions are added in the form of 0.8 to 80 mg of ZnSO$_4$.7H$_2$O as dissociable zinc compound.

13. Pharmaceutical preparation according to claim 8 which contains 80 to 320 IU of heparin, and 0.45 to 4.5 mg of zinc ions.

14. Pharmaceutical preparation according to claim 13 which additionally contains, per gram or milliliter, 0.5 to 10 mg of a surface active agent selected from polyoxyethylene sorbitan monolaurate and polyoxymethylene sorbitan monooleate.

15. Pharmaceutical preparation according to claim 13 to which the zinc ions are added in the form of 2.0 to 20 mg of ZnSO$_4$.7H$_2$O as dissociable zinc compound.

16. Pharmaceutical preparation according to claim 8 which additionally contains, per gram or milliliter, 0.2 to 50 mg of a surface active agent selected from polyoxyethylene sorbitan monolaurate and polyoxyethylene sorbitan monooleate.

17. Pharmaceutical preparation according to claim 8 which additionally contains, per gram or milliliter, 0.5 to 10 mg of a surface active agent selected from polyoxyethylene sorbitan monolaurate and polyoxyethylene sorbitan monooleate.

18. Pharmaceutical preparation according to claim 1 which contains, per gram or milliliter, 0.25 to 3 mg of an acid sulphated polysaccharide or acid sulphated polymer and 0.18 to 18 mg of zinc ions.

19. Pharmaceutical preparation according to claim 1 wherein the dissociable zinc compound is selected from the group consisting of zinc sulfate, zinc chloride, zinc acetate and zinc citrate.

20. A method for the treatment of infections caused by herpes viruses which comprises the topical administration to the infected part of the body of an animal host in need of such treatment an antivirally effective amount of a pharmaceutical preparation according to claim 1.

21. A method for the treatment of herpes genitalis which comprises the topical administration to the infected part of the body of an animal host in need of such treatment an antivirally effective amount of a pharmaceutical preparation according to claim 1.

22. A method for the treatment of herpes dermatitis which comprises the topical administration to the infected part of the body of an animal host in need of such treatment an antivirally effective amount of a pharmaceutical preparation according to claim 1.

* * * * *